US 6,554,807 B2

(12) United States Patent
Gollobin

(10) Patent No.: US 6,554,807 B2
(45) Date of Patent: Apr. 29, 2003

(54) PROTECTIVE SHEATH FOR WINGED NEEDLES

(76) Inventor: Peter Gollobin, 72 E. Second St., Mineola, NY (US) 11501

( * ) Notice: Subject to any disclaimer, the term of this patent is extended or adjusted under 35 U.S.C. 154(b) by 15 days.

(21) Appl. No.: 09/834,159

(22) Filed: Apr. 12, 2001

(65) Prior Publication Data

US 2002/0151856 A1 Oct. 17, 2002

(51) Int. Cl.[7] .................................................. A61M 5/00
(52) U.S. Cl. .......................... 604/263; 604/171; 604/177; 604/198
(58) Field of Search ................................ 604/263, 177, 604/110, 162, 165, 164, 167, 171, 178, 198

(56) References Cited

U.S. PATENT DOCUMENTS

| | | | | |
|---|---|---|---|---|
| 4,941,881 A | * | 7/1990 | Masters et al. ............. | 604/162 |
| 5,069,341 A | * | 12/1991 | Barbieri et al. ............. | 206/365 |
| 5,192,275 A | * | 3/1993 | Burns .......................... | 604/177 |
| 5,330,438 A | * | 7/1994 | Gollobin et al. ............ | 604/110 |
| 5,562,636 A | * | 10/1996 | Utterberg ..................... | 604/171 |

* cited by examiner

Primary Examiner—Patrick Brinson
(74) Attorney, Agent, or Firm—Galgano & Burke

(57) ABSTRACT

A protective sheath for covering the needle of a winged needle after use in a medical procedure. The protective sheath is slidably disposed on a tube having a hollow needle at one end and a pair of outwardly projecting flexible wings adjacent the end of the tube with the needle. The protective sheath has a hollow, generally tubular shaped body having a forward end oriented toward the needle and a rearward end oriented away from the needle. The sheath body has at least one longitudinally extending slot commencing at the forward end thereof and extending toward the rearward end for slidably receiving the wings therein to allow at least part of the sheath to be slid past the wings to cover the needle. A guard is provided at the rearward end of the sheath extending radially outwardly from the sheath and at least partially annularly around the sheath.

26 Claims, 1 Drawing Sheet

PROTECTIVE SHEATH FOR WINGED NEEDLES

FIELD OF THE INVENTION

The present invention relates generally to a protective sheath for winged needles commonly used for intravenous infusion sets, scalp-vein sets, and blood collection sets, as well as for fistula needles used in blood dialysis. More particularly, the present invention relates to an improvement to such protective sheaths.

DESCRIPTION OF THE PRIOR ART

A well known problem in the health care industry is the danger posed by accidental needlesticks from contaminated or used syringes and intravenous equipment. Health care professionals as well as maintenance personnel who dispose of used medical equipment face exposure to hepatitis, AIDS and other diseases which can be transmitted by needlesticks from such contaminated or used equipment. A solution to this problem can be found in U.S. Pat. No. 4,941,881, to Masters et al, granted Jul. 17, 1990 wherein the intravenous infusion set comprises a length of tube having a needle at one end of the tube, flexible wings adjacent the needle and a sheath slidably disposed on the tube and adapted to be slid over the needle to cover the needle after it has been used. The sheath comprises a tubular body having a longitudinally extending slot commencing at the forward end of the sheath adapted for receiving therein the wings in a folded-up configuration so as to allow at least part of the sheath to be slid past the wings to cover the needle. The sheath also includes a cutout at the rearward end of the slot for engaging the wings when they are released so as to lock the sheath in position covering the needle. In operation, following removal of the needle from the patient, the user grasps the wings together with one hand and with the other hand slides the sheath forwardly so that the wings enter the slot and are engaged in the cutout therefor and the sheath covers the needle.

An improvement to the protective sheath of the Masters et al patent can be found in U.S. Pat. No. 5,330,438, to Gollobin et al, granted Jul. 19, 1994. In the improved protective sheath of the Gollobin et al patent, there are provided at least three longitudinally extending slots commencing at the forward end of the sheath each having a width slightly less than the width of one of the wings and each terminating towards the rear of the sheath in a cutout having a width at least equal to the width of one of the wings. The sheath is provided at its rearward end with a knurled, generally cylindrical, annular base by which the sheath may be easily grasped. In operation, the user grasps the sheath at the rearward annular base thereof with one hand and pulls on the tube with the other hand to retract the needle within the sheath with each wing of the needle entering a slot and engaging a cutout to lock the sheath in position covering the needle.

SUMMARY OF THE INVENTION

It is a primary object of the present invention to further improve the protective sheaths disclosed in the above discussed U.S. Pat. Nos. 4,941,881 and 5,330,438, the subject matter of these patents being incorporated herein by reference, whereby the protection afforded against needlesticks is enhanced and the manipulation of the protective sheath in covering the used needle is facilitated.

The above object, as well as others which will hereinafter become apparent, is accomplished in accordance with the present invention by the provision of a needle set consisting of a length of tube having a needle at one end of the tube, a pair of outwardly projecting flexible wings adjacent the end of the tube with the needle and a sheath slidably disposed on the tube and adapted to be slid over the needle to cover the needle after use. The sheath is a hollow, generally tubular body having a forward end oriented toward the needle and a rearward end oriented away from the needle. The tubular body has at least one longitudinal slot and preferably at least three longitudinal slots commencing at the forward end and extending toward the rearward end for receiving the outwardly projecting flexible wings. The rear end of each slot is provided with engaging means for the outwardly projecting flexible wings in the form of cutouts so as to lock the sheath in position covering the needle after the needle has been retracted therein. The improvement consists in providing the protective sheath at or near the rearward end thereof with an outwardly projecting, at least partially annular guard. The provision of such an outwardly projecting guard at the rearward end of the protective sheath prevents the user's hand from slipping forwardly on the sheath when the user grasps the sheath and pulls the tube therethrough. This is particularly beneficial in those situations where the user is wearing latex gloves which may be slippery or wet. Furthermore, such a guard also insures that the user grasps the protective sheath at the rear thereof and not over the portion with the slot or slots which could collapse the sheath on the tube therein clamping the same and preventing movement thereof.

The foregoing and related objects are also attained with such an improved protective sheath for a wing type needle having the aforementioned construction.

BRIEF DESCRIPTION OF THE DRAWINGS

Other objects and features of the present invention will become apparent from the following detailed description considered in connection with the accompanying drawings, in which.

DESCRIPTION OF THE PREFERRED EMBODIMENT

Figure 1:
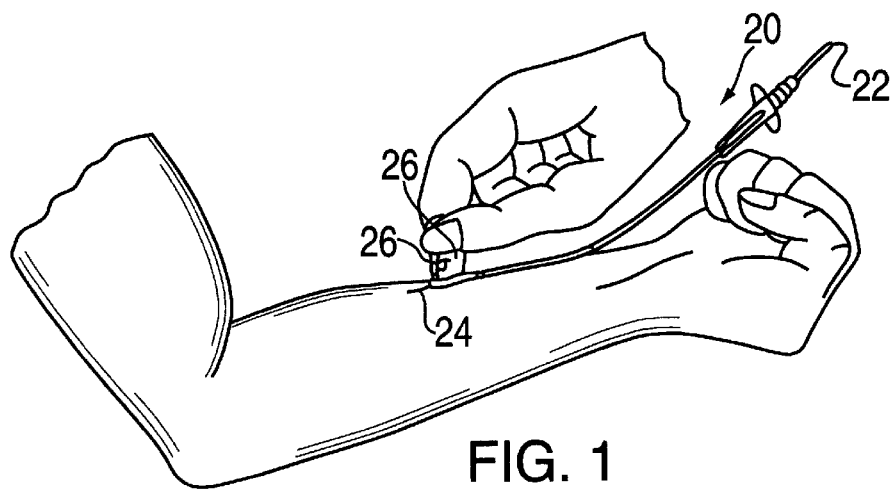
FIG. 1 is a perspective view of the intravenous infusion set being inserted or removed from the forearm of a patient with the improved protective sheath rearwardly displaced on the needle tube.
Figure 2:
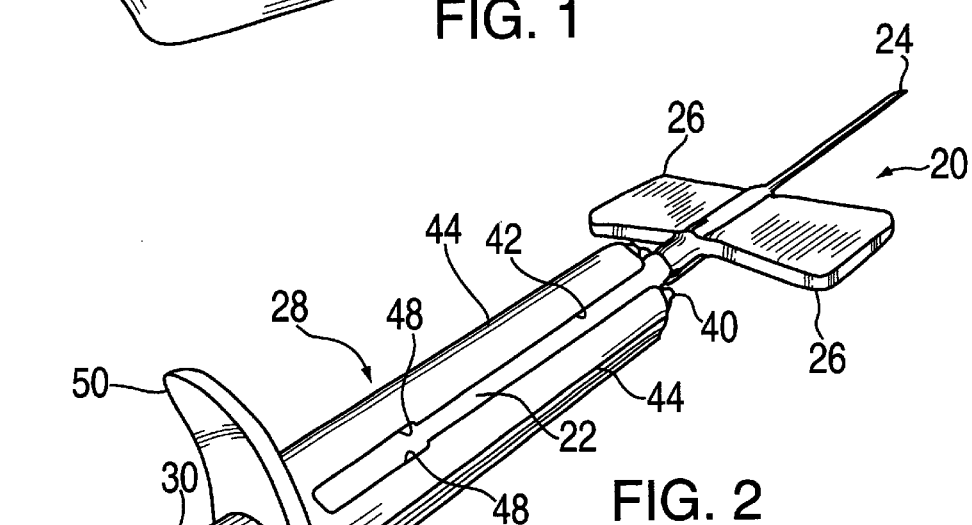
FIG. 2 is an enlarged perspective view of the intravenous infusion set and improved protective sheath showing the needle and wings immediately prior to retraction into the sheath.
Figure 3:
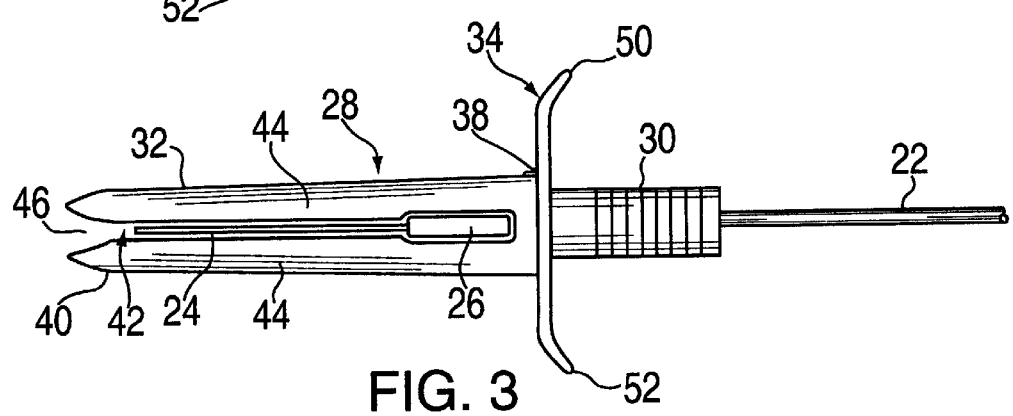
FIG. 3 is an enlarged side elevational view showing the needle and wings in a fully retracted and locked position with respect to the sheath.

Turning now to the drawings, there is shown in FIGS. 1 to 3 an intravenous or IV infusion set generally designated 20. IV infusion set 20 includes a section of tube 22 made of clear flexible plastic, a hollow metal needle 24 joined to one end of tube 22 and two outwardly projecting wings 26 preferably made of flexible plastic. Wings 26 are located adjacent needle 24. This type of IV infusion set is commonly sold under the trademark Butterfly™ infusion set. As is well known, a connector (not shown) is disposed on the end of tube 22 opposite needle 24 for connecting the IV infusion set to the appropriate medical apparatus.

IV infusion set 20 further includes a sheath, generally designated 28, slidably disposed on tube 22. Although sheath 28 is slidably disposed on the tube, before and during use of the infusion set as seen in FIG. 1, it is spaced rearwardly from wings 26 so that it does not interfere with needle 24 when the IV infusion device is in use. Of course, some means for temporarily securing sheath 28 relative to tube 22 could also be used. Sheath 28 is adapted to be slid past flexible wings 26 to cover the needle after the needle has been used. Sheath 28 includes means for locking the sheath in position covering needle 24 comprising means on the sheath for engaging wings 26. Sheath 28 is preferably formed of a clear, relatively stiff but resilient plastic material and includes a knurled, generally cylindrical, annular base, designed 30, a hollow, generally tubular shaped body, designated 32, and a guard, designated 34. Annular base 30 has a central bore 36 through which tube 22 is adapted to slidably pass and is integrally connected to the rearward end 38 of tubular shaped body 32. The forward end 40 of tubular shaped body 32 is oriented toward needle 24 while rearward end 38 is oriented away from needle 24. Tubular shaped body 32 is provided with at least one and, as disclosed in U.S. Pat. No. 5,330,438, preferably at least three longitudinally extending slots 42 extending from the forward end 40 to the rearward end 38 of body 32. Slots 42 define longitudinally extending fingers 44 in body 32 which circumscribe a central through bore 46 in body 32 which is aligned with bore 36 of base 30. Through bore 46 is adapted to permit tube 22 to slidably pass therethrough.

Each of the slots 42, when there are at least three such slots, are adapted to receive only one of the wings 26 to thereby allow at least part of sheath 28 to be slid past wings 26 to cover needle 24. The width of each slot 42 is less than the width of a single wing 26 so that fingers 44 are resiliently spread apart upon insertion therein of the wing. Cutouts 48 are formed at the rearward end of slots 42 and are adapted to receive and engage therein wings 26 to thereby lock sheath 28 in position covering needle 24. Each cutout 48 has a width approximately equal to the width of a wing 26 and a length slightly greater than the length thereof so that upon receipt of a wing 26 in a slot 42, fingers 44 will, following their resilient wedging apart, upon passage of wing 26, snap back and resume their normal position thereby restraining wings 26 in the cutouts and locking sheath 28 in position covering needle 24.

When only a single slot 42 is provided in sheath 28, as disclosed in U.S. Pat. No. 4,941,881, then the slot is dimensioned to accept the passage of the two wings 26 folded together which are released when cutout 48 is reached to substantially resume their normal configuration. Upon substantially resuming their normal "butterfly"*configuration, wings 26 are restrained by cutout 48 so that sheath 28 is locked in position covering needle 24.

Guard 34 extends radially outwardly from and at least partially annularly around sheath 28 and preferably consists of a pair of opposing tangs 50 and 52. Tangs 50 and 52 of guard 34 are formed integrally with protective sheath 28 and are disposed at the rearward end 38 thereof and preferably at the junction of annular base 30 with the rearward end 38 of tubular shaped body 32.

In operation, protective sheath 28 will normally be threaded onto tube 22 at the assembly point by the manufacturer before the butterfly needle 24, 26 is installed on tube 22. The use of IV infusion device 20 is no different than the use of the standard winged type IV infuser. The infusion device is connected to an IV apparatus and the needle is placed in the patient, as clearly seen in FIG. 1. Wings 26 prevent the sheath from interfering with the needle during use. When it is time to remove IV infusion device 20 the device is removed in the same manner as a standard type IV infuser with the assistance of wings 26.

After use by the doctor, nurse or other medical personnel, and to protect and cover a used needle, the medical professional grasps with one hand rear annular base 30 of the protective sheath and with the other hand, pulls on tube 22 until wings 26 enter and slide into different slots 42 until they are locked in place within cutouts 48 at which point the needle is fully encased within fingers 44 of protective sheath 28, as clearly seen in FIG. 3.

Guard 34 prevents the user's hand from accidentally slipping forwardly on sheath 28 while gripping base 30 and pulling tube 22 through sheath 28. Guard 34 furthermore insures that when the user grasps sheath 28 to pull tube 22 therethrough, he or she is disposed to grasp base 30 thereof rather than the portion of sheath 28 where fingers 44 are located because of the presence of the guard. Without the presence of guard 34, the user might inadvertently grasp sheath 28 at fingers 44 and collapse the same on tube 22 thereby clamping the tube and rendering it impossible to slide or pull the tube through the sheath.

It should be noted that although the illustrated embodiment shows use of the protective sheath specifically for winged needles used in IV infusion sets, it can be used for any type of winged needle, such as those used in scalp vein sets, blood collections sets and for fistula needles used in dialysis.

While only one embodiment of the present invention has been shown and described, it is to be understood that many changes and modifications may be made thereunto without departing from the spirit and scope of the following claims.

What is claimed is:

1. In a needle set of the type including a length of tube having a hollow needle at one end, a pair of outwardly projecting flexible wings adjacent the end of the tube with the needle, and a protective sheath slidably disposed on the tube and adapted to be slid over the needle to cover the needle after use, said sheath comprising a hollow, generally tubular shaped body having a forward end oriented toward the needle and a rearward end oriented away from the needle, said body having at least one longitudinally extending slot commencing at the forward end thereof and extending towards the rearward end for slidably receiving the wings therein to allow at least part of said sheath to be slid past the wings to cover the needle, the improvement comprising:

a guard at the rearward end of said sheath extending radially outwardly from said sheath and at least partially annularly around said sheath so as to prevent a user's hand which has grasped the rearward end of the sheath in order to pull the tube therethrough from sliding towards the forward end of the sheath.

2. The needle set as defined in claim 1, wherein said protective sheath further includes a generally cylindrically shaped annular base connected to the rearward end of said tubular shaped body, and said guard is disposed at the junction of said base with said body.

3. The needle set as defined in claim 2, wherein said generally tubular shaped body has at least three longitudinally extending slots commencing at the forward end thereof and extending towards the rearward end, each of said slots being adapted to slidably receive only one of said wings to allow at least part of said sheath to be slid past the wings to cover the needle.

4. The needle set as defined in claim 3, wherein said slots each have a width which is slightly less than the width of one of said wings.

5. The needle set as defined in claim 1, wherein said protective sheath further includes means for locking said sheath in position covering the needle.

6. The needle set as defined in claim 5, wherein the means for locking the sheath in position comprises means on said sheath for engaging the wings.

7. The needle set as defined in claim 6, wherein said means on said sheath for engaging the wings comprises a cutout in said slot for receiving and engaging therein said wings to lock said sheath in position covering the needle.

8. The needle set as defined in claim 3, wherein said protective sheath further includes means for locking said sheath in position covering the needle.

9. The needle set as defined in claim 8, wherein the means for locking the sheath in position comprises means on said sheath for engaging the wings.

10. The needle set as defined in claim 9, wherein said means on said sheath for engaging the wings comprises a cutout in each of said slots for receiving and engaging therein one of said wings to lock said sheath in position covering the needle.

11. The needle set as defined in claim 10, wherein each said cutout has a width at least equal to the width of one of said wings.

12. The needle set as defined in claim 1, wherein said guard comprises a pair of opposing tangs extending radially outwardly from said protective sheath.

13. The needle set as defined in claim 1 wherein said protective sheath is made from plastic.

14. A protective sheath for a winged needle having a pair of outwardly projecting flexible wings and which is attached to an end of a tube, said protective sheath being adapted to be slidably disposed on the tube and slid over the needle to cover the needle after use, said protective sheath comprising:

a hollow, generally tubular shaped body having a forward end and a rearward end, said body having at least one longitudinally extending slot commencing at the forward end thereof and extending towards the rearward end for slidably receiving the wings of said needle therein to allow at least part of said sheath to be slid past the wings to cover the needle, and a guard at the rearward end of said sheath extending radially outwardly from said sheath and at least partially annularly around said sheath, whereby when said sheath is slidably disposed on a tube and a user has grasped with a hand the rearward end of the sheath in order to pull the tube therethrough, the user's hand is prevented from sliding towards the forward end of the sheath.

15. The protective sheath as defined in claim 14, which further includes a generally cylindrically shaped annular base connected to the rearward end of said tubular shaped body, and said guard is disposed at the junction of said base with said body.

16. The protective sheath as defined in claim 15, wherein said generally tubular shaped body has at least three longitudinally extending slots commencing at the forward end thereof and extending towards the rearward end, each of said slots being adapted to slidably receive only one of said wings to allow at least part of said sheath to be slid past the wings to cover the needle.

17. The protective sheath as defined in claim 16, wherein said slots each have a width which is slightly less than the width of one of said wings.

18. The protective sheath as defined in claim 14, further includes means for locking said sheath in position covering the needle.

19. The protective sheath as defined in claim 18, wherein the means for locking the sheath in position comprises means on said sheath for engaging the wings.

20. The protective sheath as defined in claim 16, wherein said means on said sheath for engaging the wings comprises a cutout in said slot for receiving and engaging therein said wings to lock said sheath in position covering the needle.

21. The protective sheath as defined in claim 16, further includes means for locking said sheath in position covering the needle.

22. The protective sheath as defined in claim 21, wherein the means for locking the sheath in position comprises means on said sheath for engaging the wings.

23. The protective sheath as defined in claim 22, wherein said means on said sheath for engaging the wings comprises a cutout in each of said slots for receiving and engaging therein one of said wings to lock said sheath in position covering the needle.

24. The protective sheath as defined in claim 23, wherein each said cutout has a width at least equal to the width of one of said wings.

25. The protective sheath as defined in claim 14, wherein said guard comprises a pair of opposing tangs extending radially outwardly from said protective sheath.

26. The protective sheath as defined in claim 14, wherein said protective sheath is made from plastic.

* * * * *